United States Patent
Mathis et al.

(10) Patent No.: US 7,588,034 B2
(45) Date of Patent: Sep. 15, 2009

(54) THREE PIECE DRAPE WITH FLUID DIVERSION CAPABILITIES

(75) Inventors: Michael P. Mathis, Marietta, GA (US); John Rotella, Marietta, GA (US); Brian Lin, Alpharetta, GA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 314 days.

(21) Appl. No.: 10/953,655

(22) Filed: Sep. 29, 2004

(65) Prior Publication Data

US 2006/0065274 A1    Mar. 30, 2006

(51) Int. Cl.
*A61B 19/00* (2006.01)

(52) U.S. Cl. .................. 128/849; 128/850; 128/851; 128/852; 128/853; 128/854; 128/855; 128/856

(58) Field of Classification Search .......... 128/851–856
See application file for complete search history.

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,364,928 A | 1/1968 | Creager, Jr. et al. | |
| 3,502,763 A | 3/1970 | Hartmann | |
| 3,542,615 A | 11/1970 | Dobo et al. | |
| 3,668,050 A | 6/1972 | Donnelly | |
| 3,692,618 A | 9/1972 | Dorschner et al. | |
| 3,791,382 A | 2/1974 | Collins | |
| 3,802,817 A | 4/1974 | Matsuki et al. | |
| 3,849,241 A | 11/1974 | Butin et al. | |
| 3,902,484 A | 9/1975 | Winters | |
| 4,041,203 A | 8/1977 | Brock et al. | |
| 4,076,017 A | 2/1978 | Haswell | |
| 4,089,331 A | 5/1978 | Hartigan et al. | |
| 4,340,563 A | 7/1982 | Appel et al. | |
| 4,522,863 A * | 6/1985 | Keck et al. | 428/196 |
| 4,570,628 A | 2/1986 | Neal | |
| 4,873,997 A * | 10/1989 | Marshall | 128/849 |

(Continued)

FOREIGN PATENT DOCUMENTS

WO    WO 03/079919    10/2003

(Continued)

OTHER PUBLICATIONS definition of sole, panel and sleeve.*

(Continued)

*Primary Examiner*—Patricia Bianco
*Assistant Examiner*—Tarla Patel
(74) *Attorney, Agent, or Firm*—Karl V. Sidor; James Arnold; James B. Robinson

(57) ABSTRACT

A three-piece surgical drape with fluid diverting channel or sleeve therein and method of making or assembling the same. The drape generally including a first liquid impermeable section attached at either end thereof to second and third sections of the drape, respectively. At least a portion of one end of the first section of the drape folded back upon itself and intermittently tacked or bonded to the first section to create a channel or sleeve adapted to divert fluids. The channel or sleeve may also have a tube or hose placed therein to facilitate or enhance fluid diversion through the channel or fluid removal therefrom.

19 Claims, 4 Drawing Sheets

U.S. PATENT DOCUMENTS

| | | |
|---|---|---|
| 5,145,727 A | 9/1992 | Potts et al. |
| 5,169,706 A | 12/1992 | Collier, IV et al. |
| 5,178,931 A | 1/1993 | Perkins et al. |
| 5,188,885 A | 2/1993 | Timmons et al. |
| 5,222,507 A * | 6/1993 | Taylor ................... 128/849 |
| 5,345,946 A | 9/1994 | Butterworth et al. |
| 5,398,700 A | 3/1995 | Mills et al. |
| 5,464,024 A | 11/1995 | Mills et al. |
| 5,540,979 A | 7/1996 | Yahiaoui et al. |
| 5,618,278 A | 4/1997 | Rothrum |
| 5,845,641 A | 12/1998 | Pinney et al. |
| 6,199,553 B1 | 3/2001 | Hafer et al. |
| 6,213,124 B1 * | 4/2001 | Butterworth ............ 128/853 |
| 6,216,700 B1 | 4/2001 | Griesbach et al. |
| 6,615,836 B1 * | 9/2003 | Griesbach et al. ......... 128/849 |
| 6,615,837 B1 | 9/2003 | Griesbach, III |
| 2004/0098782 A1 | 5/2004 | Griesbach, III |
| 2004/0118409 A1 | 6/2004 | Griesbach, III |
| 2005/0022822 A1 * | 2/2005 | Santilli et al. ............ 128/849 |

FOREIGN PATENT DOCUMENTS

WO    WO 03/079920    10/2003

OTHER PUBLICATIONS

Method 5450, Federal Test Method Standard No. 191A, "Permeabiltiy to Air; Cloth; Calibrated Orifice Method", Jul. 1978.

\* cited by examiner

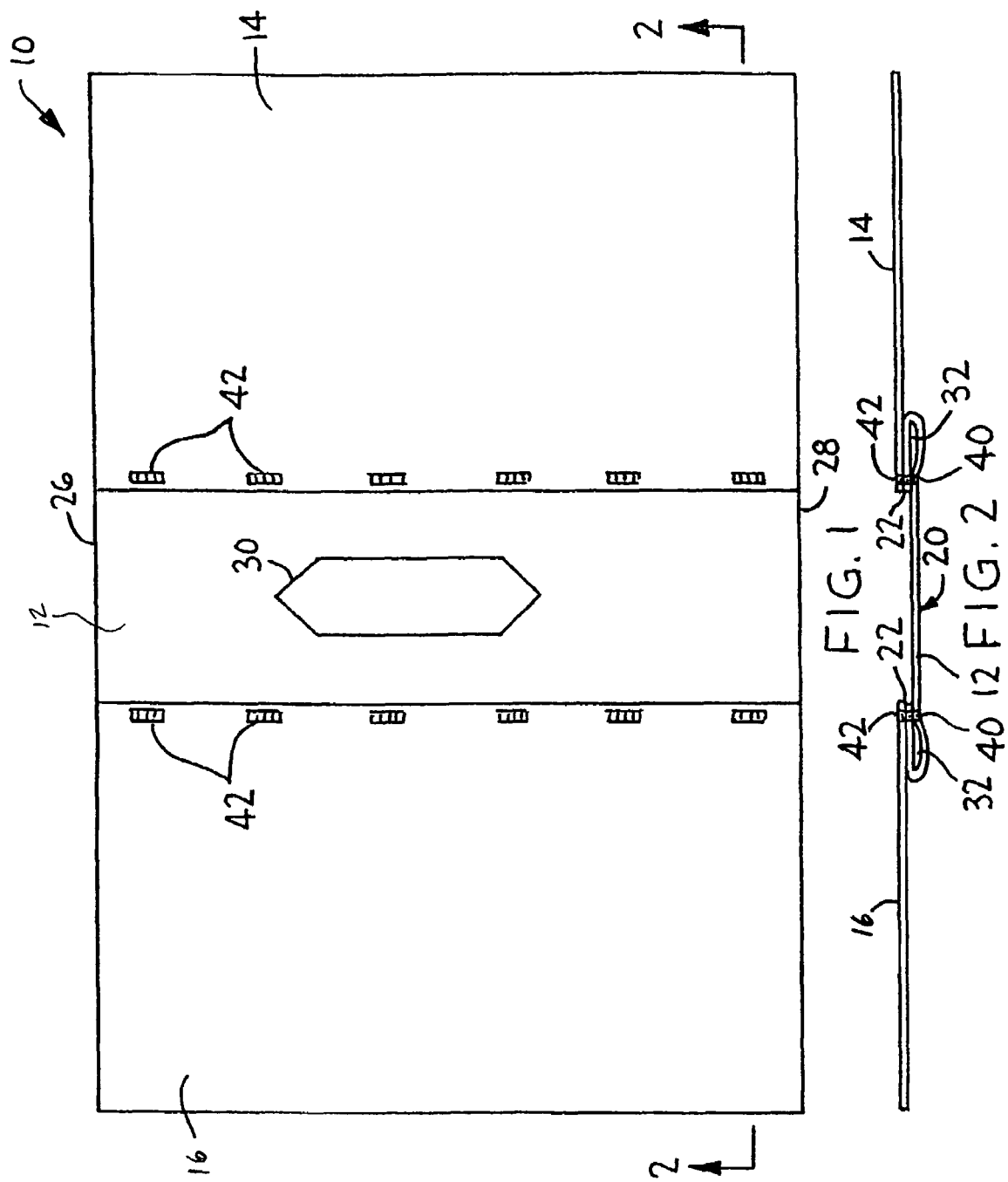

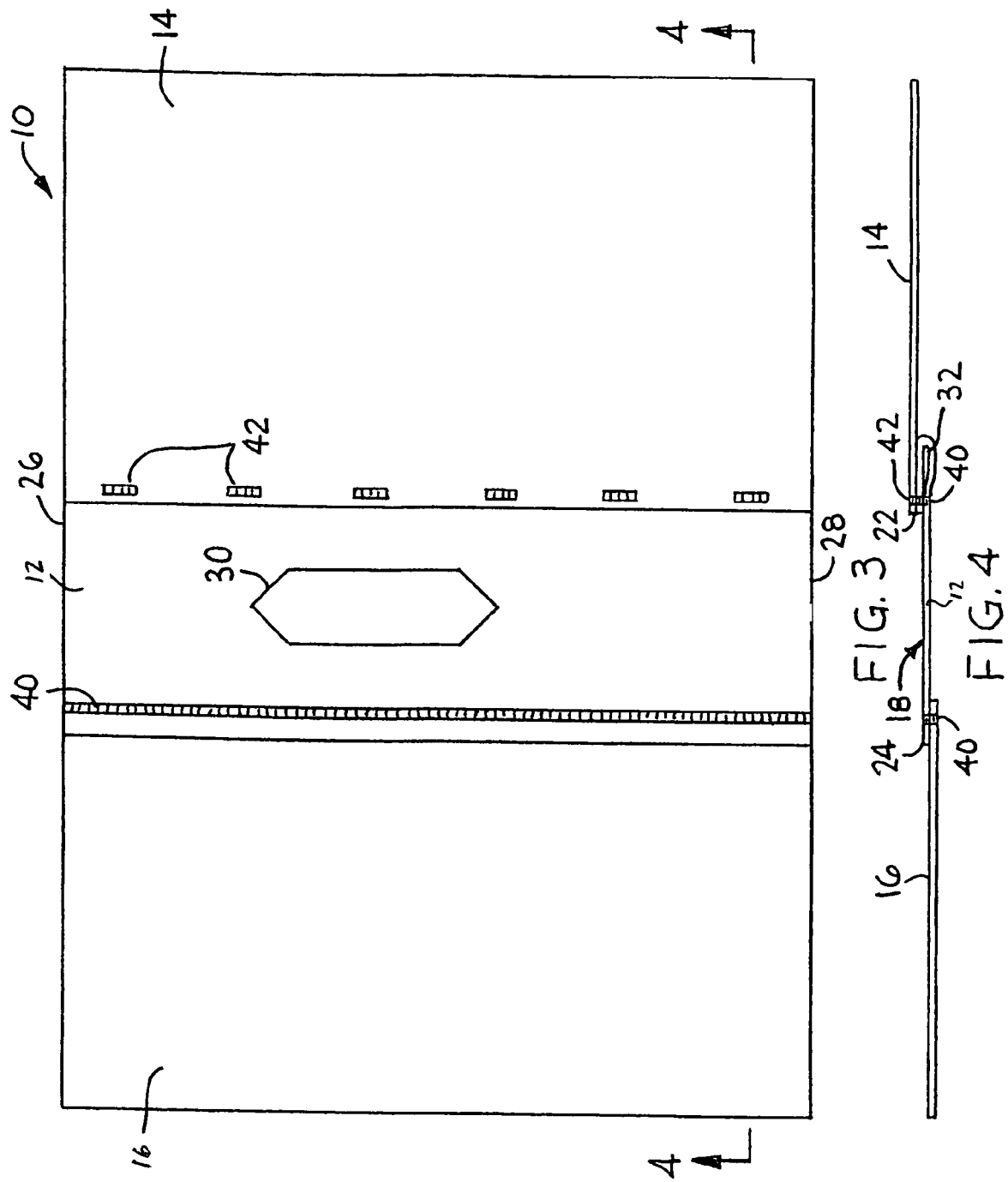

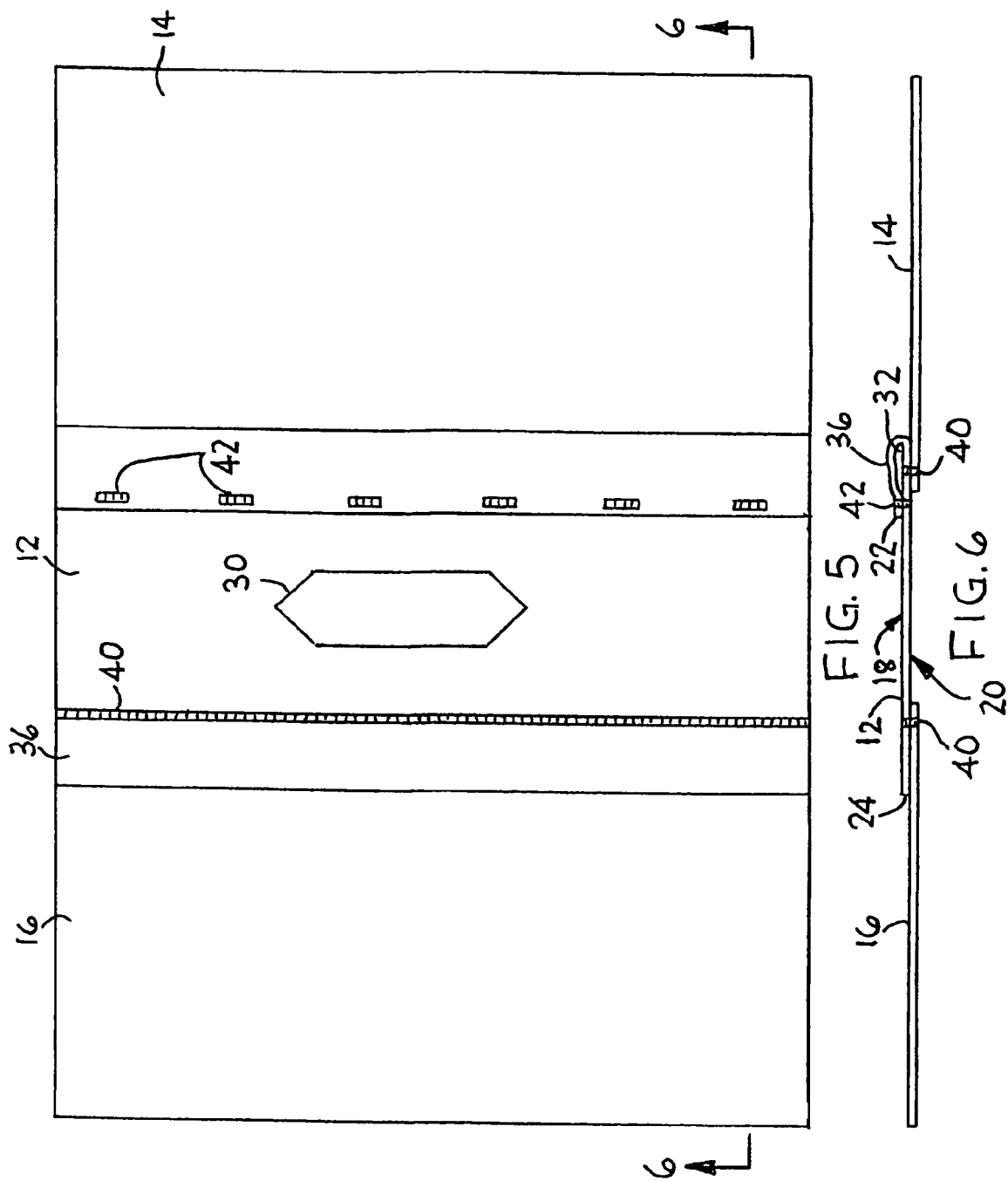

THREE PIECE DRAPE WITH FLUID DIVERSION CAPABILITIES

Drapes are used during surgical procedures, in part, to provide a sterile field about the surgical site and during other treatment procedures requiring the maintenance of a sterile environment. When used during surgery, drapes prevent blood and other bodily fluids from cross contaminating the sterile field.

A variety of surgical drapes exist, but most share several common features. Surgical drapes will have one or more openings or apertures (more commonly known in the medical field as "fenestrations") through which the surgical procedure is performed. Most drapes are made of a water-repellent or water-impermeable material, or are coated with such a material, to prevent passage of bodily fluids as well as contaminating microorganisms. Many of today's surgical drapes are made of disposable nonwoven fabrics, plastic film, or papers.

An adhesive material is normally attached to the periphery of the drape material that defines the fenestration(s) so that the drape can be held in place around the surgical site and so that blood will not pass between the drape and the patient's body. The combination of the drape itself and the adhesive material around the perimeter of the aperture ensures a barrier between the surgical wound and the remainder of the body.

During surgical procedures, fairly large amounts of bodily fluids or irrigation liquids are frequently emitted from the fenestrated operating site. If such fluids were allowed to spill over onto the surgical room floor, potentially hazardous slipping situations could occur. In addition, failure to control fluid runoff during surgery could interfere with the sterile field necessary to be maintained during the procedure and/or the ability to account for the total fluids lost during the procedure.

Various means have been developed to absorb, retain and/or collect such fluids. Early surgical procedures often involved the use of absorbent towels to square off the operating site. These towels would in turn act to absorb fluids. Gradually, the designs were improved to include absorbent materials built into the drape itself, including such materials as foam located about the fenestration. When large amounts of fluid were being used or emitted from the incision area, bags and other types of drainage apparatus were employed to channel, collect, or drain the fluids away from the operating site. Examples of such systems can be found in neurological, obstetrical (c-section) and orthopedic (arthroscopy) drapes.

Currently, both disposable non-woven as well as reusable woven surgical drapes are used to create the sterile field for operative procedures. Some drapes employ a primary base sheet in conjunction with a smaller sheet, or pad, that is often made of an absorbent material backed by a liquid impervious film. When used, the reinforcing, absorbent pad is superimposed over the larger base sheet and is often connected thereto with an adhesive. Both the base sheet and the smaller pad have one or more corresponding apertures which define the surgical sites. An example of a surgical drape with a reinforcing, absorbent pad is shown in U.S. Pat. No. 3,902,484 to Winters. If designed correctly, the absorbent area of a surgical drape facilitates cleanup and movement of the patient after the operative procedure.

Various surgical drapes have been developed which employ either an integral or an attachable pouch near the fenestration(s) to collect runoff fluids used or emitted during surgery. For example, U.S. Pat. No. 3,791,382 to Collins shows a drape useful for abdominal surgery where pouches are mounted on either side of the incision area. U.S. Pat. No. 4,089,331 to Hartigan et al. employs a drape with certain fold-back portions that form pockets near the drape fenestration. These pockets are formed on the drape for retaining fluid runoff emanating from the incision site and are not intended for high fluid flow nor are they intended to assist or enable instrument retention or line control. U.S. Pat. Nos. 3,364,928, 4,076,017, and 4,570,628 to Creager. Jr., et al., Haswell, and Neal, respectively, show the use of various fluid collection devices on drapes employed for performing various vaginal procedures. The collection devices described in these patents are typically plastic bag-like structures that are either formed integrally with, or attached separately to, the top surface of the surgical drape. U.S. Pat. No. 5,464,024 to Mills et al. illustrates another form of a collection pouch that, in some embodiments, is formed on the top surface of the surgical drape so as to completely surround the fenestration and incision site.

Finally, U.S. Pat. No. 5,618,278 to Rothrum, is illustrative of a surgical drape that employs an attachable fluid collection pouch. As shown in the figures of this patent, a collection pouch is provided with an adhesive attachment means for mounting on the top surface of a surgical drape near the fenestration. The plastic pouch has adhesive mounting strips located on its rear surface which, when release material strips covering the adhesive areas are removed, allow the pouch to be adhered to the cloth-like top surface of the surgical drape.

Problems with the adhesive attachments between plastic fluid collection pouches and the top surface of the surgical drapes are sometimes encountered when using such attachable collection pouch devices. As described above, large amounts of fluids may be used near or emitted from the surgical incision site. Often, the fluids will come into contact with the adhesive interface between the fluid collection pouch and the cloth-like absorbent top surface of the surgical drape. (Generally, the collection pouches will actually be mounted on the absorbent reinforcement pads that are mounted on the larger main panel of the surgical drape.) When this occurs, the adhesive bond between the pouch and the cloth-like surface tends to weaken and sometimes may even fail. Obviously, as the collection pouch becomes heavier due to it filling with liquids, more strength is required at the adhesive interface. If the interface completely fails, the potential exists for the pouch to disconnect from the drape and spill over onto the operating floor or otherwise destroy the sterile field. Furthermore, the pouches must be replaced when full thereby subjecting the sterile field and/or surgical environment to leakage and contamination during replacement or exchange of the pouches. As the pouches are generally located on the sides of the drapes, spillage is also likely where surgeon pushes against or leans against a filled pouch during the procedure the pouches. Even in those instances where the pouches have a drain valve, it is not uncommon for the pouches to fill significantly and experience many of the difficulties discussed above.

While numerous attempts have been made to control and/or absorb fluids which come in contact with a drape during a surgical procedure, there is still a need for a drape which exhibits an area of liquid impermeability about the surgical site, as well as possessing other areas about the area of liquid impermeability which can offer increased breathability, and therefore comfort to the patient, as well as reducing the cost of the materials for the drape.

Thus, there is still a need for further improved surgical drape designs that employ a fluid barrier which is capable of maintaining the sterile field without the need for a drape whose entire surface is covered with a film. More specifically, there is a need for a multi-section drape with continuous fluid diversion capabilities during the entire procedure without the exchange or need for exchange of pouches or the like.

SUMMARY OF THE INVENTION

In response to the difficulties and problems discussed above, a three piece surgical drape having fluid diverting channels therein has been developed.

One aspect of the present invention is directed to a drape which may be used to cover a patient during a surgical procedure. The drape includes first, second and third panels of material. The first panel has an upper surface and a lower surface, two ends, two edges, and a fenestration through which a surgical procedure may be performed when the drape is covering a patient during the surgical procedure. The second and third panels are attached on opposing ends of the first panel. The first panel being folded back on itself at at least one end thereof thereby creating a sleeve or channel which is adapted to receive and channel fluids therethrough. Each of the respective ends of the first panel which is folded back on itself in order to form the sleeve or channel being intermittently secured (e.g., embossed, bonded, or the like) to the first panel.

The channels or sleeves created at the ends of the first panel are not flat, but rather should be at least slightly open or expanded, and are adapted to divert or channel fluid therethrough. Once in the channel the fluid may be diverted to a collection container for monitoring and/or disposal. The channel or sleeve may be designed so as to be capable of receiving a tube or hose therein. Such a tube or hose can be used to divert fluid from the channel or sleeve of the drape to a collection container (not shown) for measuring and/or monitoring fluid loss or simply for disposal. Flow through such a tube may be gravity dependent or, alternatively, the tube may be connected to a vacuum or aspiration source so as to facilitate fluid removal.

The present invention is also directed to a surgical drape for covering a patient during a surgical procedure. The drape includes first, second and third sections. The first section of the drape having an upper surface and a lower surface, two ends, two edges, and a fenestration. The second section of the drape is secured to one of the ends of the first section of the drape such that at least a portion of the first section overlies a part of the second section, and a third section of the drape is secured to the second end of the first section of the drape such that at least a portion of the first section overlies a part of the third section. At least a portion of the portion of the first section overlying a part of the second section is folded back onto and intermittently bonded to the first section to create a channel adapted to divert fluids. In some aspects of the present invention, at least a portion of the portion of the first section overlying a part of the third section of material may be folded back onto and intermittently bonded to the first section to create a second channel adapted to divert fluids The present invention is also directed to a method of making a three-part drape, with fluid channels therein. The drape being adapted for covering a patient during a surgical procedure. The method generally includes the steps of: providing first, second, and third sections of material; securing the second section of material to one end of the first section of material; and securing the third section of material to the second end of the first section of material. The first section of material will generally have an upper surface and a lower surface, two ends, two edges, and a fenestration. The method further includes the step of folding a portion of the first end of the first section of material back onto another portion of the first section, and securing to the first section of material the folded over portion of the first end of the first section of material, thereby creating a channel adapted to collect and/or divert fluids which flow thereinto. The method may further include the steps of folding a portion of the second end of the first section of material back onto another portion of the first section, and securing to the first section of material the folded over portion of the second end of the first section of material, so as to create a second channel adapted to collect and/or divert fluids which flow thereinto.

The invention will be more fully understood and further features and advantages will become apparent when reference is made to the following detailed description of exemplary aspects of the invention and the accompanying drawings.

BRIEF DESCRIPTION OF THE DRAWINGS

The purpose and advantages of the present invention will be apparent to those skilled in the art from the following detailed description in conjunction with the appended drawings in which:

FIG. 1 is a top view of an aspect of a drape according to the present invention;

FIG. 2 is a cross-sectional view of the drape of FIG. 1;

FIG. 3 is an perspective view of a partially assembled drape according to an aspect of the invention, the first panel or section of the drape shown attached to the second and third panels or sections in a substantially end-to-end fashion;

FIG. 4 is a cross-sectional view of the drape of FIG. 3;

FIG. 5 is an perspective view of a partially assembled drape according to an aspect of the present invention, the first panel or section of the drape shown attached to the second and third panels or sections in a substantially overlapping fashion;

FIG. 6 is a cross-sectional view of the drape of FIG. 5; and

DETAILED DESCRIPTION OF THE PRESENT INVENTION

Figure 7:
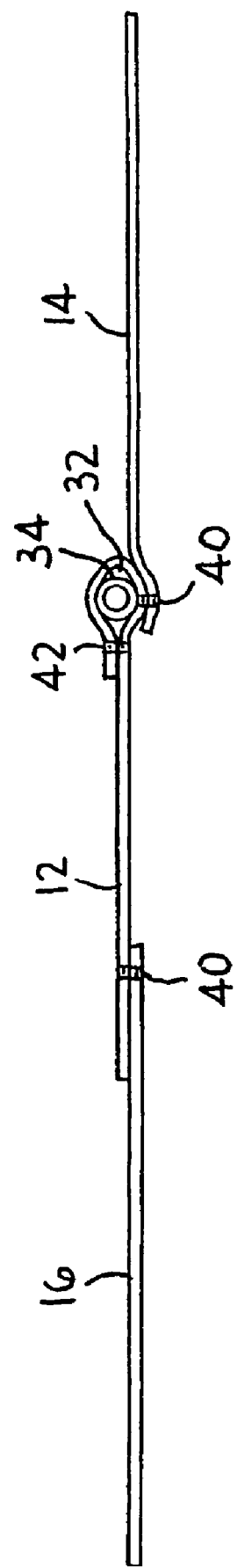
FIG. 7 is the same as that of FIG. 2, except that tube has been positioned in the sleeve thereof.

As used herein the following terms have the specified meanings, unless the context demands a different meaning, or a different meaning is expressed; also, the singular generally includes the plural, and the plural generally includes the singular unless otherwise indicated.

As used herein, all percentages, ratios and proportions are by weight unless otherwise specified.

As used herein, the terms "comprises", "comprising" and other derivatives from the root term "comprise" are intended to be inclusive or open-ended terms that specify the presence of any stated features, elements, integers, steps, or components, but do not preclude the presence or addition of one or more other features, elements, integers, steps, components, or groups thereof. Accordingly, the term "comprising" encompasses the more restrictive terms "consisting essentially of" and "consisting of."

As used herein, the term "fiber" generally refers to an elongated strand of defined length, such as staple fibers formed by cutting a continuous strand into lengths of, for example, 2 to 5 cm. Collections of fibers may have the same or different lengths.

As used herein, the term "filament" refers to a generally continuous strand that has a large ratio of length to diameter, such as, for example, a ratio of 1000 or more.

As used herein the term "meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers are microfibers which may be continuous or discontinuous, are generally smaller than 10 microns in average diameter, and are generally tacky when deposited onto a collecting surface.

As used herein the term "microfibers" means small diameter fibers having an average diameter not greater than about 75 microns, for example, having an average diameter of from about 0.5 microns to about 50 microns, or more particularly, microfibers may have an average diameter of from about 2 microns to about 40 microns. Another frequently used expression of fiber diameter is denier, which is defined as grams per 9000 meters of a fiber and may be calculated as fiber diameter in microns squared, multiplied by the density in grams/cc, multiplied by 0.00707. A lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by 0.00707. Thus, a 15 micron polypropylene fiber has a denier of about 1.42 ($15^2 \times 0.89 \times 0.00707 = 1.415$). Outside the United States the unit of measurement is more commonly the "tex", which is defined as the grams per kilometer of fiber. Tex may be calculated as denier/9.

As used herein "multilayer laminate" means a laminate having multiple layers. For example, some of the layers may be spunbond and some meltblown, such as a spunbond/meltblown/spunbond (SMS) laminate and others as disclosed in U.S. Pat. No. 4,041,203 to Brock et al., U.S. Pat. No. 5,169,706 to Collier, et al, U.S. Pat. No. 5,145,727 to Potts et al., U.S. Pat. No. 5,178,931 to Perkins et al. and U.S. Pat. No. 5,188,885 to Timmons et al. Such a laminate may be made by sequentially depositing onto a moving forming belt first a spunbond fabric layer, then a meltblown fabric layer and last another spunbond layer and then bonding the laminate. Alternatively, the fabric layers may be made individually, collected in rolls, and combined in a separate bonding step. Such exemplary fabrics usually have a basis weight of from about 0.1 to 12 osy (6 to 400 gsm), or more particularly from about 0.75 to about 3 osy. Multilayer laminates may also have various numbers of meltblown layers or multiple spunbond layers in many different configurations and may include other materials like films (F) or coform materials, e.g. spunbond-meltblown-meltblown-spunbond (SMMS), spunbond-meltblown (SM), spunbond-film-spunbond (SFS), etc.

As used herein the terms "nonwoven" and "nonwoven web" refers to a web having a structure of individual fibers, filaments or threads which are interlaid, but not in an identifiable manner as in a knitted fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

As used herein the term "spunbonded fibers" refers to small diameter fibers which are formed by extruding molten thermoplastic material as filaments from a plurality of fine, usually circular capillaries of a spinneret with the diameter of the extruded fibers then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 20 microns.

As used herein, "Frazier air permeability" or "Frazier porosity" refers to the measured value of a well-known test with the Frazier Air Permeability Tester in which the permeability of a fabric is measured as standard cubic feet of air flow per square foot of material per minute with an air pressure differential of 0.5 inches (12.7 mm) of water under standard conditions.

These terms may be defined with additional language in the remaining portions of the specification.

TEST METHODS

Frazier Porosity: A. measure of the breathability of a fabric is the Frazier Porosity which is performed according to Federal Test Standard No. 191A, Method 5450. Frazier Porosity measures the air flow rate through a fabric in cubic feet of air per square foot of fabric per minute or CFM. Convert CFM to liters per square meter per minute (LSM) by multiplying by 304.8.

It should be noted that any given range presented herein is intended to include any and all lesser included ranges. For example, a range of from 45-90 would also include 50-90; 45-80; 46-89 and the like. Thus, the range of 95% to 99.999% also includes, for example, the ranges of 96% to 99.1%, 96.3% to 99.7%, and 99.91 to 99.999%.

Reference now will be made in detail to various embodiments of the invention, one or more examples of which are set forth below. Various elements of the present invention will be given numeral designations and the invention will be discussed so as to enable one skilled in the art to make and use the invention. It should be appreciated that each example is provided by way of explaining the invention, and not as a limitation of the invention. For example, features illustrated or described with respect to one aspect may be used with another aspect to yield still a further aspect. These and other modifications and variations are contemplated to be within the scope and spirit of the invention.

In addition, the invention will be described in the context of its various configurations. It should be appreciated that alternative arrangements of the invention can comprise any combination of such configurations. As such, the use of a desired aspect for ease in understanding and describing the invention shall not, in any manner, limit the scope of the invention.

FIG. 1 illustrates a drape 10 according to the present invention. The drape 10 may be used to cover a patient during a surgical procedure. As illustrated, the drape includes first, second and third panels of material, 12, 14, and 16, respectively. The first panel has an upper surface 18 and a lower surface 20 (FIG. 2), two ends 22, 24 (FIG. 2), and two edges 26, 28. The first panel is also shown with a fenestration 30 therein through which a surgical procedure may be performed when the drape is covering a patient during the surgical procedure. The second and third panels 14, 16 are attached on opposing ends 22, 24 of the first panel 12. Although, the first panel 12 is shown as being folded back on itself at both ends 22, 24 so as to create a sleeve or channel 32 (FIG. 2) adapted to channel fluids therethrough at each end, only one sleeve or channel need be present. Each of the respective ends 22, 24 of the first panel 12 which is folded back on itself to form the sleeve or channel 32 is intermittently secured (e.g., embossed, bonded, or the like) to the first panel 12.

The first panel 12 may be secured to the second and third panels 14, 16 in a variety of manners including, for example, embossing, adhesive, heat sealing, or bonding, especially ultrasonic bonding. The first panel 12 should be attached to the second and third panels 14, 16 with a solid bond so that liquids do not pass between the panels at the point of attachment thereby avoiding contamination of the sterile field.

While the first panel 12 of the drape may be attached to the second and third panels 14, 16 in a variety of different ways, at least two techniques are thought to be most desirable. The first being that the ends of the panels are secured (e.g., bonded or the like) to each other at or near the ends thereof as shown in FIGS. 3 and 4. The first panel is then folded back upon itself to enable attachment thereof as shown on the right side of the figures. An alternate way of attaching two panels of the drape to each other is shown in FIGS. 5 and 6, wherein an end of the first panel 12 substantially overlaps a portion of the second panel 14, and the first 12 and second panel 14 are bonded or otherwise secured to one other such that a flap 36 (FIG. 6) of the first panel 12 material extends well beyond the bonding point 40 of the two panels. The flap 36 of first panel 12 may then be folded back onto itself or onto another portion of the first panel 12 and secured thereto to create a channel or sleeve 32 as described above. The latter form of attachment or securement will remove the bonding point 40 between the panels from a critical area (i.e., one that is likely to encounter significant quantities of fluid during a procedure) of the drape thereby reducing the chance or likelihood of contamination of the sterile field should the bond line be breached or otherwise compromised for any reason. The second end of the first panel 12 is shown bonded to the third panel 16 of the drape 10, but not yet tacked or otherwise bonded back onto the first panel 12 to form a second channel or sleeve 32.

The first panel should be liquid impermeable and is desirably a reinforced fluid impermeable material such as a film laminate. An absorbent backed by a liquid impervious film is generally contemplated such that some liquids can be absorbed about the surgical site, yet the film backing prevents the liquids from passing entirely through first panel and contacting the patient or otherwise contaminating the sterile field. Suitable film laminates generally include, but are not limited to, film/meltblown, film/spunbond, foam/film, film/SM, film/SMS, etc. Desired laminates include, but are not limited to, those available from Kimberly-Clark Corporation under the tradenames Control (a foam/film laminate described in U.S. Pat. No. 3,668,050), and Control+(a bicomponent SB/MB/film laminate described in U.S. Pat. No. 5,540,979), each of which are incorporated herein in their entirety for all purposes.

It is contemplated the drape, and more specifically each of its panels, may be of various sizes and shapes. It is further contemplated that the fenestration 30 could have various other shapes, or that multiple fenestrations could be present in a particular drape.

The present invention is unlike other previous drapes in that the drape need not be constructed of a single sheet of material or one laminate and need not incorporate a film over the entire drape. Furthermore, the second and third panels of the present invention may be constructed of a breathable material. Further, as the area below the table top level is generally not part of the sterile field, only a moderate level of barrier, if any, is necessary in this area. The ability to reduce the amount of film in a drape as compared to prior drapes allows for additional breathability, a softer drape, more drapeability, lighter overall drape weight, and a quieter drape, as well as a reduction in material costs, each of which can be beneficial. Desirably, the second and third panels of the drape will be constructed of nonwoven materials or a combination thereof, such as SMS or the like. A material which exhibits a Frazier Porosity of at least 20 CFM, and more desirably at least 30 CFM is desirable for the side panels of the drape. It is further contemplated that while the second and third materials are not intended to absorb large quantities of fluids and in fact may be hydrophobic in some instances, the second and third panels could be constructed of material that will provide for some absorption in the event liquids come in contact therewith. In at least one aspect of the present invention it is contemplated that the side panels of the drape may be treated with chemicals or treatments known to those of skill in the art to achieve a certain level of absorbent capability.

As best illustrated in FIGS. 2, 4 and 6, the channels or sleeves 32 created at the ends 22, 24 of the first panel are not or should not be flat, but rather are at least slightly open or expanded or can be opened or expanded, and are adapted to divert or channel fluid therethrough. That is, while the fold, pleat, or rounded end at the end of each channel or sleeve 32 forms a barrier to fluid run-off, the channel or sleeve 32 is sufficiently open or openable so as to readily receive fluids therein. Once in the channel 32 the fluid may be diverted to a collection container for monitoring and/or disposal. The channel or sleeve 32 may be designed to be capable of receiving a tube or hose therein. Such a tube or hose 34 as illustrated in FIG. 7, can be used to divert fluid from the channel or sleeve 32 of the drape 10 to a collection container (not shown) for measuring and/or monitoring fluid loss or simply for disposal. Flow through such a tube may be gravity dependent or, alternatively, the tube may be connected to a vacuum or aspiration source so as to facilitate fluid removal. The tube 34 may have multiple openings therein to facilitate liquid flow into the tube 34 from different locations of the channel or sleeve 32. It will be appreciated that the maximum size of the tube which may be used therein will be limited by the size of the channel or sleeve 32, whether the tube is placed in the channel or sleeve 32 prior to or after the first panel 12 is secured (e.g., bonded, etc.) to itself, and if after bonding of the first panel to itself, then upon the frequency of the bond points 42.

The intermittent bond points 42 can also assist with instrument retention or line control. That is, whether a tube (such as that shown at 34 in FIG. 7) is present or not, another instrument (not shown) may be passed through a section of the intermittently bonded first panel 12 such that a portion of the instrument or a line or hose connected thereto is retained therein. For example, the instrument could be passed through one end of the channel and between two of the intermittent bond points 40 on the first panel 12 so that the instrument or an attached control line is retained by the drape. The ability to retain an instrument or line connected thereto can provide for easy access to a frequently used instrument and/or keep instrument lines which might otherwise clutter the surgical area or become tangled neatly contained.

The present invention is also directed to a surgical drape for covering a patient during a surgical procedure. The drape includes first, second and third sections. The first section of the drape having an upper surface and a lower surface, two ends, and two edges. The first section also having an opening or fenestration therein through which a surgical procedure may be performed when the drape is covering a patient during the surgical procedure. The second section of the drape is secured to one of the ends of the first section of the drape such that at least a portion of the first section substantially overlies a part of the second section, and a third section of the drape is secured to the second end of the first section of the drape such that at least a portion of the first section substantially overlies a part of the third section. At least a portion of the portion of the first section overlying a part of the second end of the first section is folded back onto and intermittently bonded to the first section to form a channel adapted to divert fluids.

As noted above the first section of the drape may be secured to the second and third sections of the drape in a variety of fashions. Desirably the first section is secured to the second and third sections via a solid bond. A solid bond between the first section and the other sections of the drape will prevent liquid leakage therebetween and will reduce the chance of contamination of the sterile field. The channel created may be sized to accommodate the placement of a tube positioned within at least a portion of one of the channels, the tube being adapted to allow fluid removal therethrough. As above, the channel may also be used to assist with instrument retention and/or line control.

The present invention is also directed to a method of making a three-part drape, with fluid channels therein. The drape being adapted for covering a patient during a surgical procedure. The method generally includes the steps of: providing first, second, and third sections of material; securing the second section of material to one end of the first section of material; and securing the third section of material to the second end of the first section of material.

The first section of material having an upper surface and a lower surface, two ends, and two edges. The first section further includes a fenestration therein through which a surgical procedure may be performed when the drape is covering a patient during the surgical procedure. The method further includes the step of folding a portion of the first end of the first section of material back onto another portion of the first section, and securing to the first section of material the folded over portion of the first end of the first section of material, in such a way as to create a channel adapted to channel or divert fluids which flow therethrough.

The method may further include the steps of folding a portion of the second end of the first section of material back onto another portion of the first section, and securing to the first section of material the folded over portion of the second end of the first section of material to create a second channel adapted to collect and/or divert fluids which flow thereinto. As shown in FIGS. 5 and 6, the step of securing the second section 14 of material to one end 22 of the first section 12 of material may include bonding the first section 12 of material to the second section 14 of material in such a manner that the first section 12 overlaps the second section 14 so as to create a flap 36 of first section 12 material having an end 24. The steps of folding a portion of the first end 22 of the first section 12 of material back onto another portion of the first section 12, and securing to the first section 12 of material the folded over portion of the first end 22 of the first section 12 of material, so as to create a channel 32 adapted to divert fluids which flow thereinto, may include folding the flap 36 of first section 12 material back onto the flap (a portion of the first material) or onto another portion of the first section 12 material and intermittently bonding or otherwise securing the flap 36 to the another portion of the first section 12 material such that the channel 32 is adapted to receive, collect, and/or divert fluids which flow thereinto.

Similarly, the step of securing the third section 16 of material to one end 24 of the first section 12 of material may include bonding the first section 12 of material to the third section 16 of material such that the first section 12 overlaps the third section 16 so as to create a flap 36 of first section 12 material having an end. The steps of folding a portion of the second end 24 of the first section 12 of material back onto another portion of the first section 12, and securing to the first section 12 of material the folded over portion of the end 24 of the first section 12 of material, so as to form a second channel adapted to collect and/or divert fluids which flow thereinto, may include folding the flap 36 of first section 12 material back onto the flap 36 or onto another portion of the first section 12 material and intermittently bonding the flap 36 to the another portion of the first section 12 material such that the second channel is adapted to receive fluids therein.

While the invention has been described in detail with respect to specific aspects thereof, those skilled in the art, upon obtaining an understanding of the invention, may readily conceive of alterations to, variations of, and equivalents to the described aspects and the processes for making them. The invention may be embodied in other specific forms without departing from the scope and spirit of the inventive characteristics thereof. The present aspects therefore are to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. A surgical drape for covering a patient during a surgical procedure, the drape comprising:
 a multipanel drape, the multipanel drape having:
  a first panel of material having an upper surface and a lower surface, two ends, and two edges, the first panel having a fenestration therein through which the surgical procedure is performed when the drape covers a patient during the surgical procedure;
  a second panel having an end disposed in contiguous, abutting relationship to one end of the first panel, the end of the second panel being attached to the one end of the first panel; and
  a third panel having an end disposed in contiguous, abutting relationship to an opposite end of the first panel, the end of the third panel being attached to the opposite end of the first panel such that the second panel and the third Panel are completely separated by the first panel; and
 a sleeve defined in the first panel of the drape, the sleeve being defined by folding and intermittently bonding an end of the first panel back onto itself, the sleeve further defining openings between the intermittent bond locations for receiving fluid into the sleeve,
 wherein the sleeve is adapted to receive and channel fluids therethrough to a collection container adapted to measure fluid loss, monitor fluid loss, or dispose of fluids.

2. The drape of claim 1, wherein a second sleeve is defined in the first panel, the second sleeve being defined by folding and intermittently bonding an end of the first panel opposite a first sleeve back onto itself, the second sleeve further defining openings between the intermittent bond locations for receiving fluid into the second sleeve.

3. The drape of claim 1, wherein the first panel is a film laminate.

4. The drape of claim 3, wherein the film laminate is liquid impermeable.

5. The drape of claim 1, wherein the second and third panels comprise at least in part a nonwoven material.

6. The drape of claim 5, wherein the nonwoven material is selected from a group comprising spunbond, meltblown, film, foams, or combinations thereof.

7. The drape of claim 1, further comprising a tube positioned within at least a portion of the sleeves so as to allow fluid removal therethrough.

8. The surgical drape of claim 1, wherein the multipanel drape consists essentially of a first panel, a second panel and a third panel.

9. A surgical drape for covering a patient during a surgical procedure, the drape comprising:
- a multi-section drape, the multi-section drape having:
  - a first section having an upper surface and a lower surface, two ends, and two edges, the first section having a fenestration therein through which the surgical procedure is performed when the drape covers a patient during the surgical procedure;
  - a second section having an end disposed in contiguous, generally abutting relationship to one end of the first section of the drape, such that a portion of the end of the first section overlies and is secured to a portion of the end of the second section; and
  - a third section having an end disposed in contiguous, generally abutting relationship to the opposite end of the first section of the drape, such that a portion of the end of the first section overlies and is secured to a portion of the end of the third section whereby the second section and the third section are completely separated by the first section of the drape; and
- a sleeve defined by the first section of the drape, the sleeve being defined by folding and intermittently bonding an end of the first section back onto itself, the sleeve further defining openings between the intermittent bond locations for receiving fluid into the sleeve,
- wherein the sleeve is adapted to receive and divert fluids to a collection container adapted to measure fluid loss, monitor fluid loss, or dispose of fluids.

10. The drape of claim 9, wherein a second sleeve is defined in the first section, the second sleeve being defined by folding and intermittently bonding an end of the first section opposite a first sleeve back onto itself, the second sleeve further defining openings between the intermittent bond locations for receiving fluid into the second sleeve.

11. The drape of claim 10, further comprising a tube positioned within at least a portion of the second channel, the tube being adapted to allow fluid removal therethrough.

12. The drape of claim 9, wherein the end of the first section overlaying and secured to the second and third sections are secured via a solid bond.

13. The drape of claim 9, wherein the first section is a film laminate.

14. The drape of claim 9, wherein the second and third sections have a Frazier porosity of at least 20 CFM, and desirably at least 30 CFM.

15. The drape of claim 9, wherein the film laminate is liquid impermeable.

16. The drape of claim 9, wherein the second and third sections comprise at least in part a nonwoven material.

17. The drape of claim 16, wherein the nonwoven material is selected from a group comprising spunbond, meltblown, foams, or combinations thereof.

18. The drape of claim 9, further comprising a tube positioned within at least a portion of the first channel, the tube being adapted to allow fluid removal therethrough.

19. The surgical drape of claim 9, wherein the multi-section drape consists essentially of a first section, a second section and a third section.

* * * * *